US006541663B2

(12) United States Patent
Siebenhaar et al.

(10) Patent No.: US 6,541,663 B2
(45) Date of Patent: Apr. 1, 2003

(54) PROCESS FOR PREPARATION OF AMINOCARBOXYLIC ACIDS

(75) Inventors: Bernd Siebenhaar, Kandern-Wollbach (DE); Milos Rusek, Binningen (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 09/872,653

(22) Filed: Jun. 1, 2001

(65) Prior Publication Data

US 2002/0099246 A1 Jul. 25, 2002

Related U.S. Application Data

(63) Continuation of application No. PCT/EP99/09267, filed on Nov. 29, 1999.

(30) Foreign Application Priority Data

Dec. 1, 1998 (CH) ................................ 2387/98

(51) Int. Cl.⁷ ...................... C07C 51/16; B01J 25/00; B01J 21/02; B01J 27/06; B01J 21/14
(52) U.S. Cl. .............. 562/523; 562/552; 502/202; 502/208; 502/224; 502/232; 502/301
(58) Field of Search ................ 502/301, 202, 502/208, 224, 232; 562/553, 523

(56) References Cited

U.S. PATENT DOCUMENTS

| 3,928,441 A | 12/1975 | Hunter et al. |
| 5,292,936 A | 3/1994 | Franczyk |
| 5,739,390 A * | 4/1998 | Franczyk et al. |

FOREIGN PATENT DOCUMENTS

| EP | 0 506 973 | 10/1992 |
| GB | 642 861 | 9/1950 |

OTHER PUBLICATIONS

Bashkirov et al, The Preparation of Higher Ketones by Dehydrogenation of Secondary Alcohols on Copper–Chromium and Nickel–Chromium Catalysts, 1964, Neftekhimiya, 4(2), pp. 298–300. Abstract.*

Katona et al, Amorphous Alloy Catalysis. VII. Activation and Surface Characterization of an Amorphous Cu–Ti Alloy Catalyst Precursor in the Dehydrogenation of 2–Propanol and Comparison with Cu–Zr, 1995, Journal of Catalysis, 153, pp. 333–343.*

* cited by examiner

Primary Examiner—Samuel Barts
Assistant Examiner—Paul A. Zucker
(74) Attorney, Agent, or Firm—William A. Teoli, Jr.; Thomas Hamilton

(57) ABSTRACT

Raney copper, which is doped (promoted) with an effective quantity of a doping (promoting) agent selected from the group boric acid, onium fluorides, salts of fluorine complex anions, and heteropoly acids, represents an outstanding oxidation catalyst for amine-group-containing primary amines to carboxylic acids.

10 Claims, No Drawings

PROCESS FOR PREPARATION OF AMINOCARBOXYLIC ACIDS

This Application is a continuation of PCT/EP99/09267, filed Nov. 29, 1999.

The present invention relates to a process for the production of amine-group-containing carboxylic acid salts by oxidation of corresponding primary alcohols in an aqueous alkaline medium at an elevated temperature in the presence of a modified Raney copper catalyst.

In WO 92/06069, O. Gomez et al. describe the oxidation of ethanol amines to carboxylic acids, whereby the reaction is carried out in an aqueous-alkaline medium in the presence of Raney copper as the oxidation catalyst. In order to be able to reuse the catalyst in further reaction cycles, it must be reactivated, in this case by treatment with formic acid and then thorough washing with demineralised water and sodium hydroxide solution. Nevertheless, repeated usage is restricted because the catalyst has too short a service life and deactivates continuously.

In WO 94/24091, it is proposed that these disadvantages are remedied by doping (promoting) Raney copper with 10 to 50,000 ppm of an element or a metal, for example titanium, niobium, vanadium, molybdenum, manganese, nickel, lead and in particular chromium. The activity of the catalyst is only reduced thereby to a negligible extent. However, catalyst deactivation can be substantially improved. Of course, there is nothing to prevent the doping (promoting) metals, which are recognised as toxic, from reaching the reaction product, and after lengthy usage, the catalyst can no longer be reused. Simple reactivation is likewise impossible owing to the presence of doping (promoting) metals.

It has now surprisingly been found that the catalyst activity can be increased, the selectivity is maintained, the deactivation is only slight and, if necessary, can be eliminated by simple treatment with the doping (promoting) agent, and in this way multiple reusage in further reaction cycles is possible, and increased activity is observed in part during reusage, if the doping (promoting) agent employed is an ecologically acceptable agent, for example boric acid, onium fluorides or salts with fluorine complex anions, or heteropoly acids.

It was also surprisingly found that by adding adjuvants which contain carbaldehyde groups to the aqueous alkaline reaction medium, the catalyst activity and thus the reaction rate can be increased.

A first object of the invention is Raney copper, which is doped (promoted) with an effective quantity of a doping (promoting) agent selected from the group boric acid, onium fluorides, salts of fluorine complex anions, and heteropoly acids.

Effective quantity means that a minimum quantity is used and the effects are generally not further improved beyond the upper limit of a preferred quantity range. The minimum quantity, based on Raney copper, is preferably 10 ppm, more preferably 20 ppm and most preferably 50 ppm, and the maximum quantity is preferably 10,000 ppm, more preferably 8000 ppm and most preferably 5000 ppm.

Boric acid $H_3BO_3$ can be used as such in the treatment of Raney copper, or can be produced in the reaction medium from boric acid esters.

The onium fluorides in question may be, for example, unsubstituted or substituted phosphonium fluorides and more preferably ammonium fluorides. They may correspond to formula I, $$R_3XH^+\!\!-\!\!F^- \qquad (I)$$

wherein X is N or P and the symbols R are identical or different and signify H, $C_1$–$C_{20}$-alkyl, $C_2$–$C_{20}$-hydroxyalkyl, $C_1$–$C_4$-alkoxy-$C_2$–$C_{12}$-alkyl, $C_2$–$C_8$-cycloalkyl, $C_6$–$C_{10}$-aryl, $C_7$–$C_{12}$-aralkyl or $C_8$–$C_{12}$-alkaralkyl.

R may be linear or branched alkyl, which preferably contains 1 to 12, more preferably 1 to 8, most preferably 1 to 4 carbon atoms. Examples are methyl, ethyl, and the isomers of propyl, butyl, pentyl, hexyl, heptyl, octyl, decyl, dodecyl, tetradecyl, hexadecyl, octadecyl and eicosyl. Alkyl is preferably linear and preferably denotes methyl, ethyl, n-propyl and n-butyl.

R may be linear or branched hydroxyalkyl, which preferably contains 2 to 12, more preferably 2 to 8, most preferably 2 to 4 carbon atoms. Examples are hydroxyethyl, hydroxypropyl and hydroxybutyl.

R as alkoxyalkyl preferably signifies $C_1$–$C_4$-alkoxy-$C_2$–$C_4$-alkyl, whereby alkoxy is most preferably methoxy or ethoxy. Preferred examples are methoxyethyl and ethoxyethyl.

R as cycloalkyl preferably contains 4 to 7, most preferably 5 or 6 ring carbon atoms. Examples of cycloalkyl are cyclopropyl, cyclobutyl, cyclopentyl, cyclohexyl, cycloheptyl and cyclooctyl. Cyclohexyl is especially preferred.

R as aryl may be naphthyl and preferably phenyl.

R as aralkyl is preferably phenylalkyl. Examples are benzyl and β-phenylethyl.

R as alkaralkyl preferably signifies alkylbenzyl, examples being methylbenzyl, dimethyl-benzyl, trimethylbenzyl and ethylbenzyl.

X in formula I preferably signifies N.

One preferred group of compounds of formula I is that in which the symbols R are identical and are selected from the group H and $C_1$–$C_4$-alkyl. The compound of formula I in question is most preferably $NH_4F$.

Of the salts of fluorine complex anions, the alkali metal salts and onium salts are preferred in particular. Alkali metal salts are preferably, for example, lithium, sodium and potassium salts. Onium cations have already been described for the fluorides. The alkali metal salts may correspond to formula II, $$Me^+Y^- \qquad (II),$$

wherein $Me^+$ is $NH_4^+$ or an alkali metal cation, preferably $Li^+$, $Na^+$ und $K^+$, and $Y^-$ signifies a perfluorine complex anion from the group $BF_4^-$, $AlF_4^-$, $PF_6^-$, $AsF_6^-$, $SbF_6^-$ or $BiF_6^-$. Preferred compounds are $NaBF_4$, $KBF_4$, $NaPF_6$, $KPF_6$ and especially $NH_4BF_4$ and $NH_4PF_6$.

The heteropoly acids are preferably derived from the poly-acid-forming elements W, Mo and V, whereby the polyanions contain elements from the groups P, B, Si and Ge. Heteropoly acids are known and are described for example by I. V. Kozhevnikov in Uspekhi Khimii Volume 56, pages 1417 to 1443 (1987). Preferred heteropoly acids correspond to formula III, $$H_n(ZM_{12}O_{40}) \qquad (III),$$

wherein Z is P, B, Si or Ge, M is a metal from the group W, Mo and V, and n is an integer from 3 to 6. Preferred examples are $H_3[P(W_{12}O_{40})]$, $H_4[P(W_{12}O_{40})]$ and $H_5[B(W_{12}O_{40})]$.

The carbaldehyde-group-containing adjuvants are derived e.g. from formaldehyde, paraformaldehyde, the aliphatic $C_1$–$C_{12}$-alkylcarbaldeydes, aromatic carbaldehydes and the corresponding dicarbaldehydes, whereby the aromatic rings may be substituted by $C_1$–$C_6$-alkyl or by OH. Of these, $C_1$–$C_8$-alkylcarbaldehydes, benzaldehyde, cuminaldehyde and 4-hydroxybenzaldehyde are preferred for example.

These carbaldehyde-group-containing adjuvants are conveniently employed in an amount ranging from 0.1 mol % to 50 mol %, preferably 1 mol % to 20 mol %, most preferably 2 mol % to 10 mol %, based on the primary amino alcohols of formula IV.

Production of the catalysts may take place in known manner, whereby an aqueous suspension of Raney copper is mixed with an aqueous solution of the modifying agent, the mixture is stirred or left to stand for a while, and then the impregnated Raney copper is filtered off or decanted and dried. The catalyst may also be produced and used in situ, whereby the aqueous mixture comprising catalyst and modifying agent is used directly after impregnation for the oxidation of primary alcohols. The catalyst may be used repeatedly. What is particularly advantageous here is that, when a loss of activity is first observed, further modifying agent is dispensed into the reaction mixture, and the loss of activity can be significantly to totally eliminated. In general, activated Raney copper is used for the modification. This is available commercially. Activation of Raney copper may be carried out whereby commercial Raney copper is treated for ca. 2 hours at a temperature of for example 200° C. with a mixture of nitrogen and hydrogen (volume ratio for example 4:1), and is then cooled under a protecting gas (for example argon).

A further object of the invention is a process for the production of amine-group-containing carboxylic acid salts by oxidation of amine-group-containing primary alcohols in an aqueous-alkaline reaction medium, in the presence of a modified Raney copper catalyst and at elevated temperature, the process being characterised in that the Raney copper is doped (promoted) with an effective quantity of a modifying agent selected from the group boric acid, onium fluorides, salts of fluorine complex anions and heteropoly acids.

The above-described embodiments and preferences apply to the modified Raney copper. The catalyst may be employed in a quantity of 0.1 to 30% by weight, preferably 0.5 to 20% by weight, more preferably 0.5 to 15% by weight, most preferably 1 to 10% by weight, based on the primary alcohol.

The reaction temperature may be for example from 80 to 300° C., preferably from 100 to 250 ° C.

The reaction is advantageously carried out under excess pressure. The pressure may be, for example, from 1 to 50 bars, preferably 2 to 25 bars, most preferably 5 to 15 bars.

The reaction is carried out in an alkaline reaction medium, preferably in the presence of NaOH or KOH. The amount of alkali base in the reaction mixture is advantageously calculated such that at least equal molar amounts of alkali base are present in relation to the primary amine. It is appropriate to use an excess of alkali base, for example one to five times, preferably up to three times, most preferably up to double the molar excess.

The amines may contain 1 to 3 primary alcohol groups, and the amines may be primary, secondary or tertiary amines.

The amine-group-containing primary alcohols may corresponds, for example, to formula IV,

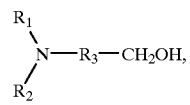

(IV)

wherein $R_1$ and $R_2$, independently of one another, are H, linear or branched, $C_1$–$C_{18}$-alkyl either unsubstituted or substituted by F, Cl, Br, —$NH_2$, $C_1$–$C_4$-alkoxy, $C_1$–$C_4$-halogenalkyl or —COOH; $C_3$–$C_8$-cycloalkyl, $C_6$–$C_{10}$-aryl or $C_7$–$C_{12}$-aralkyl either unsubstituted or substituted by F, Cl, Br, —$NH_2$, $C_1$–$C_4$-alkyl, $C_1$–$C_4$-alkoxy, $C_1$–$C_4$-halogenalkyl; phosphonomethyl; $R_1$ and $R_2$ together are tetramethylene or pentamethylene; or $R_1$ and $R_2$, independently of one another, have the significance $R_3$—$CH_2OH$; and $R_3$ is linear or branched $C_1$–$C_{17}$-alkylene which is uninterrupted or is interrupted by $C_3$–$C_8$-cycloalkyl or $C_6$–$C_{10}$-aryl.

$R_1$ and $R_2$ as alkyl preferably contain 1 to 12, more preferably 1 to 8, most preferably 1 to 4 carbon atoms. Examples and preferences of alkyl have already been described.

$R_1$ and $R_2$ as cycloalkyl preferably contain 4 to 7, most preferably 5 or 6 ring carbon atoms. Examples of cycloalkyl are cyclopropyl, cyclobutyl, cyclopentyl, cyclohexyl, cycloheptyl and cyclooctyl. Cyclohexyl is especially preferred.

$R_1$ and $R_2$ as aryl may be naphthyl and preferably phenyl.

$R_1$ and $R_2$ as aralkyl are preferably phenylalkyl. Examples are benzyl and β-phenylethyl.

$R_3$ as alkylene preferably contain 1 to 12, more preferably 1 to 8, most preferably 1 to 4 carbon atoms. Examples of alkylene are methylene, 1,1- or 1,2-ethylene, 1,1-, 1,2- or 1,3-propylene, 1,1-, 1,2-, 1,3- or 1,4-butylene, 1,1-, 1,2-, 1,3-, 1,4- or 1,5-pentylene, 1,1-, 1,2-, 1,3-, 1,4-, 1,5- or 1,6-hexylene, 1,1-, 1,2-, 1,3-, 1,4-, 1,5-, 1,6- or 1,7-heptylene, 1,1-, 1,2-, 1,3-, 1,4-, 1,5-, 1,6-, 1,7- or 1,8-octylene, nonylene, decylene, undecylene, dodecylene, tridecylene, tetradecylene, pentadecylene, hexadecylene and heptadecylene.

The group —$R_3CH_2OH$ preferably signifies 4-hydroxybutyl, 3-hydroxypropyl and most preferably 2-hydroxyethyl.

One preferred sub-group of compounds of formula IV corresponds to formula IVa,

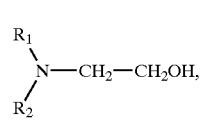

(IVa)

wherein $R_1$ and $R_2$, independently of one another, signify H or unsubstituted or —$NH_2$— or —COOH-substituted $C_1$–$C_{12}$-Alkyl or —$CH_2CH_2$—OH.

In formula IVa, $R_1$ and $R_2$, independently of one another, preferably signify H, $C_1$–$C_4$-alkyl or —$CH_2$—$CH_2$—OH. Another preferred sub-group is compounds of formula IVa, in which $R_1$ is —$CH_2CH_2$—OH and $R_2$, independently of one another, are H, $C_1$–$C_4$-alkyl or —$CH_2$—$CH_2$—OH.

Some examples of compounds of formula IV are ethanolamine, diethanolamine, triethanolamine, N-methylethanolamine, N-dimethylethanolamine, N-methyldiethanolamine, N-ethylethanolamine, N-(n-propyl)ethanolamine, N-(n-propyl)ethanolamine, N-(n-butyl)ethanolamine, N-(n-pentyl)ethanolamine, N-(n-hexyl)ethanolamine, N-(n-octyl)ethanolamine, N-(n-decyl)ethanolamine, N-(n-dodecyl)ethanolamine, N-(n-tetradecyl)

ethanolamine, N-(n-hexadecyl)ethanolamine, N-(n-octadecyl)ethanolamine, N-(di-n-propyl)ethanolamine, N-(di-n-butyl)ethanolamine, N-(di-n-hexyl)ethanolamine, 3-hydroxypropylamine, di-(3-hydroxypropyl)amine, tri-(3-hydroxypropyl)amine, 4-hydroxybutylamine, di-(4-hydroxybutyl)amine, tri-(4-hydroxybutyl)amine, 5-hydroxypentylamine, di-(5-hydroxypentyl)amine, tri-(5-hydroxypentyl)amine, 6-hydroxyhexylamine, di-(6-hydroxyhexyl)amine, tri-(6-hydroxyhexyl)amine, 8-hydroxyoctylamine, di-(8-hydroxyoctyl)amine, tri-(8-hydroxyoctyl)amine, 12-hydroxydodecylamine, di-(12-hydroxydodecyl)amine, tri-(12-hydroxydodecyl)amine, 18-hydroxyoctadecylamine, N-methyl-(3-hydroxypropyl)amine, N-methyl-(4-hydroxybutyl)amine, N-methyl-(6-hydroxyhexyl)amine, (2-aminoethyl)ethanolamine, di-(2-aminoethyl)ethanolamine, phosphonomethylethanolamine, diphosphonomethylethanolamine.

The compounds of formula IV are known, are partly commercially available or may be produced by processes that are similar to those described in literature.

The process according to the invention may be carried out, for example, in such a way that the catalyst is placed in an autoclave, then first of all the primary alcohol is added, optionally in water, followed by the alkali lye, the autoclave is sealed and the reaction mixture stirred, and the reaction is commenced whilst heating. The reaction generally continues until the hydrogen generation is no longer observed. The catalyst can be decanted from the cooled reaction mixture and used for the next reaction. The alkali metal salts of carboxylic acids that are formed may be isolated and optionally purified in the usual manner. The salts may also be converted into the free carboxylic acids and derivatives thereof, such as acid amides and acid esters. The process according to the invention is suitable for production on an industrial scale.

The aminocarboxylic acids that may be produced according to the invention can be used for many purposes. Glycine is employed for food production. Aminocarboxylic acids are known complexing agents, which are used in the detergent industry and in water treatment. In addition, the amino alcohols may be used in the production of ionic surfactants. The amino alcohols are also valuable intermediates in the production of pharmaceutical and pesticidal compositions.

The following examples illustrate the invention more fully.

EXAMPLE 1

Oxidation of Diethanolamine a) Preparation of the Catalyst

A suspension of 8.26 g of activated Raney copper in 20 ml of water is stirred with 1.0 g of a 10% solution of $NH_4B_4$ in water, and then left to stand for 15 minutes. The whole mixture is subsequently transferred to a 300 ml nickel autoclave.

b) Oxidation of Diethanolamine

To the catalyst are added 42.8 g of diethanolamine (0.4 moles), 20 ml of water and 38 g of NaOH (0.95 moles) in the form of a 50% aqueous solution. Afterwards, heating is effected to 160° C. (9.5 bars, pressure regulating valve) and stirring takes place until the hydrogen generation is no longer observed (200 minutes). The yield of iminodiacetic acid disodium salt according to NMR analysis is more than 99% by weight.

c) Reuse of the Catalyst

The autoclave containing the reaction mixture is cooled to 100° C. The supernatant solution is suctioned off through a riser, and the modified Cu catalyst remains in the autoclave. Then, diethanolamine and NaOH are added in the above-described proportions and reacted under the specified conditions. Up to the fifth reuse, the catalyst shows only slight activity loss (290 minutes, 92% by weight), and selectivity is maintained. Renewed impregnation with $NH_4BF_4$ gives a catalyst with the original high activity and selectivity.

EXAMPLE 2

Oxidation of Diethanolamine a) Preparation of the Catalyst

A suspension of 8.26 g of activated Raney copper in 20 ml of water is stirred with 0.25 g of $H_3(PW_{12}O_{40})$ in 20 ml of water, and then left to stand for 15 minutes. The whole mixture is subsequently transferred to a 300 ml nickel autoclave.

b) Oxidation of Diethanolamine

To the catalyst are added 42.8 g of diethanolamine (0.4 moles), 20 ml of water and 33.6 g of NaOH (0.84 moles) in the form of a 50% aqueous solution. Afterwards, heating is effected to 160° C. (9.5 bars, pressure regulating valve) and stirring takes place until the hydrogen generation is no longer observed (3 hours). The yield of iminodiacetic acid disodium salt according to NMR analysis is 97% by weight.

c) Reuse of the Catalyst

The autoclave containing the reaction mixture is cooled to 100° C. The supernatant solution is suctioned off through a riser, and the modified Cu catalyst remains in the autoclave. Then, diethanolamine and NaOH are added in the above-described proportions and reacted under the specified conditions. Up to the eighth reuse, the catalyst shows only slight activity loss (5 hours, 89% by weight), and selectivity is maintained. Renewed impregnation with $H_3(PW_{12}O_{40})$ gives a catalyst with the original high activity and selectivity (12th reuse, 3.5 hours, 91% by weight).

EXAMPLE 3

Oxidation of Diethanolamine a) Preparation of the Catalyst

A suspension of 8.26 g of activated Raney copper in 20 ml of water is stirred with 0.25 g of $NH_4F$ in 20 ml of water, and then left to stand for 15 minutes. The whole mixture is subsequently transferred to a 300 ml nickel autoclave.

b) Oxidation of Diethanolamine

To the catalyst are added 42.8 g of diethanolamine (0.4 moles), 20 ml of water and 33.6 g of NaOH (0.84 moles) in the form of a 50% aqueous solution. Afterwards, heating is effected to 160° C. (9.5 bars, pressure regulating valve) and stirring takes place until the hydrogen generation is no longer observed (4 hours). The yield of iminodiacetic acid disodium salt according to NMR analysis is 98% by weight.

c) Reuse of the Catalyst

The autoclave containing the reaction mixture is cooled to 100° C. The supernatant solution is suctioned off through a riser, and the modified Cu catalyst remains in the autoclave. Then, diethanolamine and NaOH are added in the above-described proportions and reacted under the specified conditions. Up to the twentieth reuse, the catalyst shows only slight activity loss (5 hours, 87% by weight), and selectivity is maintained. Renewed impregnation with $NH_4F$ or dispensing in $NH_4F$ during the reaction gives a catalyst with the original high activity and selectivity (21st reuse, 4 hours, 91% by weight).

EXAMPLE 4

Oxidation of Diethanolamine with the Addition of Benzaldehyde or 4-hydroxybenzaldehyde a) Preparation of the Catalyst A suspension of 8.26 g of activated Raney copper in 20 ml of water is stirred with 0.25 g of NH$_4$F in 20 ml of water, and then left to stand for 15 minutes. The whole mixture is subsequently transferred to a 300 ml nickel autoclave.

b) Oxidation of Diethanolamine

To the catalyst are added 42.8 g of diethanolamine (0.4 moles), 4.25 g of benzaldehyde or 4.9 g of 4-hydroxybenzaldehyde, 20 ml of water and 33.6 g of NaOH (0.84 moles) in the form of a 50% aqueous solution. Afterwards, heating is effected to 160° C. (or 180° C.) (9.5 bars, pressure regulating valve) and stirring takes place until the hydrogen generation is no longer observed.

| Addition | Temperature (° C.) | Duration of reaction (mins.) |
|---|---|---|
| benzaldehyde | 160 | 210 |
| benzaldehyde | 180 | 67 |
| 4-hydroxybenzaldehyde | 160 | 210 |
| 4-hydroxybenzaldehyde | 180 | 53 |
| none | 160 | 270 |

The yield of iminodiacetic acid disodium salt according to NMR analysis is 97–98% by weight.

c) Reuse of the Catalyst

The autoclave containing the reaction mixture is cooled to 100° C. The supernatant solution is suctioned off through a riser, and the modified Cu catalyst remains in the autoclave. Then, diethanolamine, 4-hydroxybenzaldehyde (or benzaldehyde) and NaOH are added in the above-described proportions and reacted under the specified conditions. Up to the twentieth reuse, the catalyst shows only slight activity loss, and selectivity is maintained. Renewed impregnation with NH$_4$F or dispensing in NH$_4$F during the reaction gives a catalyst with the original high activity and selectivity (21st reuse, duration of reaction 72 minutes, yield 92% by weight).

What is claimed is:

1. Raney copper, which is doped with an effective quantity of a doping agent selected from the group boric acid, onium fluorides, salts of fluorine complex anions, and heteropoly acids.

2. Raney copper according to claim 1, in which the minimum quantity of doping agent is 10 ppm, based on the Raney copper.

3. Raney copper according to claim 1, in which the maximum quantity of doping agent is 10000 ppm, based on the Raney copper.

4. Raney copper according to claim 1, in which the onium fluorides correspond to formula I, $$R_3XH^+F^- \qquad (I),$$

wherein X is N or P and the symbols R are identical or different and signify H, $C_1$–$C_{20}$-alkyl, $C_2$–$C_{20}$-hydroxyalkyl, $C_1$–$C_4$-alkoxy-$C_2$–$C_{12}$-alkyl, $C_2$–$C_8$-cycloalkyl, $C_6$–$C_{10}$-aryl, $C_7$–$C_{12}$-aralkyl or $C_8$–$C_{12}$-alkaralkyl.

5. Raney copper according to claim 4, whereby the compound of formula I is NH$_4$F.

6. Raney copper according to claim 1, whereby the salts of fluorine complex anions are alkali metal salts of formula II, $$Me^+Y^- \qquad (II),$$

wherein $Me^+$ is $NH_4^-$ or an alkali metal cation, and $Y^-$ signifies a perfluorine complex anion from the group $BF_4^-$, $AlF_4^-$, $PF_6^-$, $AsF_6^-$, $SbF_6^-$ or $BiF_6^-$.

7. Raney copper according to claim 1, whereby the heteropoly acids are those of formula III, $$H_n(ZM_{12}O_{40}) \qquad (III),$$

wherein Z is P, B, Si or Ge, M is a metal from the group W, Mo and V, and n is an integer from 3 to 6.

8. A process for the production of amine-group-containing carboxylic acid salts by oxidation of amine-group-containing primary alcohols in an aqueous-alkaline reaction medium, in the presence of a modified Raney copper catalyst and at elevated temperature, whereby the Raney copper is doped with an effective quantity of a modifying agent selected from the group boric acid, onium fluorides, salts of fluorine complex anions and heteropoly acids.

9. Process according to claim 8, in which the catalyst is used in a quantity of 0.1 to 30% by weight, based on the primary alcohol.

10. Process according to claim 8, in which the amine-group-containing primary alcohols correspond to formula IV,

wherein R$_1$ and R$_2$, independently of one another, are H, linear or branched, $C_1$–$C_{18}$-alkyl either unsubstituted or substituted by F, Cl, Br, —NH$_2$, $C_1$–$C_4$-alkoxy, $C_1$–$C_4$-halogenalkyl or —COOH; $C_3$–$C_8$-cycloalkyl, $C_6$–$C_{10}$-aryl or $C_7$–$C_{12}$-aralkyl either unsubstituted or substituted by F, Cl, Br, —NH$_2$, $C_1$–$C_4$-alkyl, $C_1$–$C_4$-alkoxy, $C_1$–$C_4$-halogenalkyl; phosphonomethyl; R$_1$ and R$_2$ together are tetramethylene or pentamethylene; or R$_1$ and R$_2$, independently of one another, have the significance R$_3$—CH$_2$OH; and R$_3$ is linear or branched $C_1$–$C_{17}$-alkylene which is uninterrupted or is interrupted by $C_3$–$C_8$-cycloalkyl or $C_6$–$C_{10}$-aryl.

* * * * *